(12) United States Patent
Gerlitz (10) Patent No.: US 10,379,341 B2
(45) Date of Patent: *Aug. 13, 2019

(54) MULTIPLE APERTURE HAND-HELD LASER THERAPY APPARATUS

(71) Applicant: MEDICAL COHERENCE LLC, Fairfield, NJ (US)

(72) Inventor: Yonatan Gerlitz, Herzliya (IL)

(73) Assignee: Medical Coherence LLC, Fairfield, NJ (US)

( * ) Notice: Subject to any disclaimer, the term of this patent is extended or adjusted under 35 U.S.C. 154(b) by 238 days.

This patent is subject to a terminal disclaimer.

(21) Appl. No.: 15/413,959

(22) Filed: Jan. 24, 2017

(65) Prior Publication Data

US 2017/0235131 A1 Aug. 17, 2017

Related U.S. Application Data

(63) Continuation of application No. 13/873,602, filed on Apr. 30, 2013, now Pat. No. 9,553,422.

(51) Int. Cl.
*G02B 27/00* (2006.01)
*A61N 5/06* (2006.01)
(Continued)

(52) U.S. Cl.
CPC ........... *G02B 27/0025* (2013.01); *A61N 5/06* (2013.01); *A61N 5/0616* (2013.01); *B23K 26/0006* (2013.01); *B23K 26/0096* (2013.01); *B23K 26/0648* (2013.01); *B23K 26/702* (2015.10); *G02B 27/30* (2013.01); *H01S 3/13* (2013.01); *H01S 5/005* (2013.01); *A61B 18/203* (2013.01);
(Continued)

(58) Field of Classification Search
CPC .......... A61N 5/0616; A61N 2005/0644; A61N 2005/067; A61N 2005/0651; A61N 2005/0659; G02B 27/0025; G02B 27/30; B23K 26/0648

See application file for complete search history.

(56) References Cited

U.S. PATENT DOCUMENTS 4,538,895 A 9/1985 Higgins et al.
4,753,521 A 6/1988 Deserno
(Continued)

FOREIGN PATENT DOCUMENTS

CN 1901968 A 1/2007
CN 102314091 A 1/2012
(Continued)

OTHER PUBLICATIONS

Candian Intellectual Property Office; Office Action for Application No. 2,769,837 dated Apr. 11, 2017.
(Continued)

*Primary Examiner* — Nathan J Jenness
(74) *Attorney, Agent, or Firm* — Randall Danskin P.S.

(57) ABSTRACT

A hand-held therapeutic laser apparatus with a special opto-mechanical construction, which enables changeability of a front collimating lens to create different effective laser apertures. A smaller effective aperture has a comparatively higher radiant flux density for treatment of a small area that requires a higher energy dose, while a larger effective aperture facilitates treatment of a large area at a relatively reduced radiant intensity.

11 Claims, 7 Drawing Sheets

(51) Int. Cl.
| | |
|---|---|
| *G02B 27/30* | (2006.01) |
| *A61B 18/20* | (2006.01) |
| *A61B 17/00* | (2006.01) |
| *A61B 18/00* | (2006.01) |
| *A61N 5/067* | (2006.01) |
| *H01S 3/13* | (2006.01) |
| *B23K 26/00* | (2014.01) |
| *B23K 26/06* | (2014.01) |
| *B23K 26/70* | (2014.01) |
| *H01S 5/00* | (2006.01) |
| *B23K 103/00* | (2006.01) |

(52) U.S. Cl.
CPC ............ *A61B 2017/00017* (2013.01); *A61B 2017/00747* (2013.01); *A61B 2018/00452* (2013.01); *A61B 2018/00636* (2013.01); *A61B 2018/00642* (2013.01); *A61B 2018/2025* (2013.01); *A61N 2005/067* (2013.01); *A61N 2005/0644* (2013.01); *A61N 2005/0651* (2013.01); *A61N 2005/0659* (2013.01); *B23K 2103/32* (2018.08)

(56) References Cited

U.S. PATENT DOCUMENTS

| | | | |
|---|---|---|---|
| 4,979,180 | A | 12/1990 | Muncheryan |
| 5,147,349 | A | 9/1992 | Johnson et al. |
| 5,208,701 | A | 5/1993 | Maeda |
| 5,259,380 | A | 11/1993 | Mendes et al. |
| 5,272,716 | A | 12/1993 | Soltz et al. |
| 5,344,434 | A | 9/1994 | Talmore |
| 5,464,436 | A | 11/1995 | Smith |
| 5,663,828 | A | 9/1997 | Knowles |
| 5,872,354 | A | 2/1999 | Hanson |
| 5,941,837 | A | 8/1999 | Amano et al. |
| 6,013,096 | A | 1/2000 | Tucek |
| 6,069,748 | A | 5/2000 | Bietry |
| 6,108,138 | A | 8/2000 | Ophey et al. |
| 6,267,779 | B1 | 7/2001 | Gerdes |
| 6,306,160 | B1 | 10/2001 | Nidetzky |
| 6,358,272 | B1 | 3/2002 | Wilden |
| 6,612,719 | B2 | 9/2003 | Richardson et al. |
| 6,746,473 | B2 | 6/2004 | Shanks et al. |
| 7,118,563 | B2 | 10/2006 | Weckwerth et al. |
| 7,374,569 | B2 | 5/2008 | Whatcott et al. |
| 7,465,307 | B2 | 12/2008 | Connors et al. |
| 7,479,137 | B2 | 1/2009 | Yamazaki et al. |
| 7,524,328 | B2 | 4/2009 | Connors et al. |
| 9,553,422 | B2 * | 1/2017 | Gerlitz ............... A61N 5/0616 |
| 9,946,082 | B2 * | 4/2018 | Gerlitz ............... A61N 5/0616 |
| 2002/0068926 | A1 | 6/2002 | Ota et al. |
| 2002/0173833 | A1 | 11/2002 | Korman et al. |
| 2003/0058916 | A1 | 3/2003 | Tanaka et al. |
| 2003/0170586 | A1 | 9/2003 | Cozean et al. |
| 2003/0233138 | A1 | 12/2003 | Spooner |
| 2004/0158301 | A1 | 8/2004 | Tucek et al. |
| 2005/0053106 | A1 | 3/2005 | Herron et al. |
| 2005/0131499 | A1 | 6/2005 | Shanks et al. |
| 2006/0095099 | A1 | 5/2006 | Shanks et al. |
| 2006/0129211 | A1 | 6/2006 | Canitano et al. |
| 2006/0206173 | A1 | 9/2006 | Gertner et al. |
| 2006/0206176 | A1 | 9/2006 | Shanks et al. |
| 2006/0224218 | A1 | 10/2006 | Tucek et al. |
| 2007/0121069 | A1 | 5/2007 | Andersen et al. |
| 2007/0185552 | A1 | 8/2007 | Masotti et al. |
| 2007/0198004 | A1 | 8/2007 | Altshuler et al. |
| 2008/0027518 | A1 | 1/2008 | Island et al. |
| 2008/0058783 | A1 | 3/2008 | Altshuler et al. |
| 2008/0077198 | A1 | 3/2008 | Webb et al. |
| 2008/0091179 | A1 | 4/2008 | Durkin et al. |
| 2008/0091249 | A1 | 4/2008 | Wang |
| 2008/0125835 | A1 | 5/2008 | Laurent |
| 2008/0215123 | A1 | 9/2008 | Maricle et al. |
| 2008/0310166 | A1 | 12/2008 | Chinniah et al. |
| 2009/0073824 | A1 | 3/2009 | Kurozuka et al. |
| 2009/0105791 | A1 | 4/2009 | McGinnis et al. |
| 2010/0053070 | A1 | 3/2010 | Tsai et al. |
| 2011/0032960 | A1 | 2/2011 | Gerlitz |
| 2013/0041431 | A1 | 2/2013 | Gerlitz et al. |
| 2013/0317571 | A1 | 11/2013 | Gerlitz |

FOREIGN PATENT DOCUMENTS

| | | |
|---|---|---|
| CN | 102573991 A | 7/2012 |
| EP | 1210905 A2 | 6/2002 |
| JP | H0199576 A | 4/1989 |
| JP | 2003066368 | 3/2003 |
| JP | 2004538108 | 12/2004 |
| JP | 2005518255 | 6/2005 |
| JP | 2006518610 | 8/2006 |

OTHER PUBLICATIONS

U.S. Patent and Trademark Office, Non-Final Office Action for U.S. Appl. No. 12/534,878 dated Jul. 12, 2012.
U.S. Patent and Trademark Office, Non-Final Office Action for U.S. Appl. No. 12/534,878 dated Feb. 28, 2013.
U.S. Patent and Trademark Office, Non-Final Office Action for U.S. Appl. No. 12/534,878 dated Jun. 17, 2013.
U.S. Patent and Trademark Office, Final Office Action for U.S. Appl. No. 12/534,878 dated Jan. 6, 2014.
Japan Patent Office; Office Action for Japanese Patent Application No. 2012-523429 dated Jan. 13, 2015.
International Search Report and the Written Opinion of the International Search Authority for Application No. PCT/IB14/01638 dated Feb. 24, 2015.
U.S. Patent and Trademark Office, Office Action for U.S. Appl. No. 14/341,153 dated May 19, 2015.
International Bureau; IPRP for Application No. PCT/IB2014/001638 dated Nov. 12, 2015.
U.S. Patent and Trademark Office, Office Action for U.S. Appl. No. 13/873,602 dated Nov. 25, 2015.
International Search Report and the Written Opinion of the International Search Authority for Application No. PCT/US2015/065079 dated Feb. 26, 2016.
Korean Intellectual Property Office; Office Action for U.S. Appl. No. 10-2012-7005632, dated Jul. 22, 2016.
Canadian Intellectual Property Office; Office Action for Application No. 2,769,837, dated Apr. 12, 2016.
European Patent Office; Extended European Search Report for Application No. 14794429.2, dated Oct. 19, 2016.
European Patent Office; Supplementary Search Report for Application No. 14794429.2, dated Nov. 7, 2016.
The State Intellectual Property Office of China; First Office Action for Application No. 201480030065.9, dated Jan. 16, 2017.

* cited by examiner

MULTIPLE APERTURE HAND-HELD LASER THERAPY APPARATUS

CROSS-REFERENCE TO RELATED APPLICATIONS

This application is a continuation of U.S. patent application Ser. No. 13/873,602, filed Apr. 30, 2013, entitled "Multiple Aperture Hand-Held Laser Therapy Apparatus," and is related to U.S. patent application Ser. No. 12/534,878, filed Aug. 4, 2009, entitled "Handheld Low-Level Laser Therapy Apparatus," both of which are incorporated herein by reference.

BACKGROUND OF THE INVENTION

Field of the Invention (Technical Field)

The present invention relates generally to a hand-held low energy laser apparatus for treating human and animal patients, and more particularly to such an apparatus having changeable lens mounting assemblies to permit adjustment of the effective aperture of the laser.

Background Art

The use of laser light to treat people and animals is known. Since the early history of mankind people have used the light from the sun to help cure ailments. In the mid-20th century attempts were made to use concentrated light to treat wounded soldiers during World War II. In later years, the laser, which is based on the quantum phenomenon of stimulated emission, provided an excellent source of concentrated coherent light for treating patients. The laser allows the therapeutic use of a selected intensity of a monochromatic and essentially coherent light beam. Such coherent light beams have been found to be effective in treating people for various ailments.

The use of a carefully selected wavelength, generally coherently directed toward a person, provides energy for selectively stimulating processes in living cells. This can help increase blood flow, excite cell activity, and intensify inter-cell communications. Laser light treatments have been applied to various ailments. Applications include various skeletal and tissue pains and injuries, such as: rheumatic and/or chronic joint inflammation; sports injuries, wounds and fresh scars; lower and upper back pain; neck pains; plantar fasciitis and sprains; tennis elbow; Achilles tendon infection; carpal tunnel syndrome; and lymphedema and edema. The treatment has also been employed in medical dermatology, such as acne, burns, scars, hemorrhoids, vitiligo (discolored skin), and herpes simplex. Lasers also find use in medical aesthetics, including the treatment of aging and dermatolysis of the face, wrinkles, sensitive skin, post-pregnancy, stretch marks, and the like. Other applications include veterinary, dental, acupuncture, and other possibilities.

The use of laser light in therapy has been shown to reduce pain, induce anti-inflammatory activity, induce healing processes and induce skin rejuvenation. In the past, light therapy has been applied by large, expensive and hazardous equipment which requires operation by trained personnel. Thus miniature, user safe laser therapy devices, which can be used at home, are desirable. No known hand-held device, however, enables changes in the aperture, the treated area, and the radiant power.

Against the foregoing background, the present invention was developed.

SUMMARY OF THE INVENTION (DISCLOSURE OF THE INVENTION)

The present invention suggests low-cost solutions for readily changing the effective aperture and radiant power of a hand-held laser apparatus, which changes can be made by the consumer-user.

A hand-held therapeutic laser apparatus with a special opto-mechanical construction, which enables changeability of a front collimating lens to create different effective laser apertures. A smaller effective aperture has a comparatively higher radiant flux density for treatment of a small area that requires a higher energy dose, while a larger effective aperture facilitates treatment of a large area at a relatively reduced radiant intensity.

The hand-held apparatus is an eye-safety laser device, and remains eye-safe during the process of changing the aperture. In one of the embodiments, the laser apparatus uses the natural divergence of the laser diode, which enables changing the front lens length with different sizes, focal lengths and distances from the laser source. The output beam in all cases is an essentially coherent beam. According to another embodiment, a laser diode beam correction lens is attached to the laser diode, then a diverging lens is used to create a beam divergence, and then the front lens creates again an essentially coherent beam, which is changeable to a variety of apertures, focal lengths and distances from the divergence lens. This latter embodiment suggests a more complicated apparatus than the first mentioned embodiment, but offers better coherence of the output beam. Eye safety is maintained with all lenses, and of course as well as without the front lens, during the process of changing the front lens.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating preferred embodiments of the invention, and are not to be construed as limiting the invention. Further, all dimensions seen in the drawings are exemplary and not limiting of the scope of the invention. In the drawings.

DESCRIPTION OF THE PREFERRED EMBODIMENTS (BEST MODES FOR CARRYING OUT THE INVENTION)

There is disclosed hereby a portable therapeutic laser apparatus. The apparatus and system according to this disclosure are adapted to exploit the natural divergence of the laser beam emitted by the laser diodes known for use in small medical devices. The laser beam, such as an infrared beam, emitted by such diodes ordinarily diverges at angles in relation to the axial direction of beam transmission. For example, if the diode is "aimed" in a direction to emit a beam having a horizontal axis of beam transmission, the initially emitted beam will have a vertical angle of divergence in a vertical plane and a horizontal angle of divergence in the horizontal plane (such planes can be visualized as intersecting along the axis of beam transmission). One of the angles of divergence typically is substantially larger than the other; whether the vertical or the horizontal angle is the greater depends upon the spatial orientation of the diode. Rotation of the diode on the axis of beam transmission likewise rotates the angles of divergence.

The instant invention exploits these angles of beam divergence by using one or more lenses to subtend and intercept the diverging beam. A lens is provided that is shaped and sized to intercept both (or all) principle angles of divergence. For example, in some embodiments, an elongated toroidal lens is employed. (A toroidal, or toric, lens has a surface which forms a portion or portions of toric surfaces.) The lens is positioned, relative to the laser diode, such that the lens's major dimension is aligned with the diode's larger angle of divergence and its minor dimension is aligned with the smaller angle of divergence. The lens is sized thus to intercept at least a substantial majority if not all the divergent beam, thereby to allow the diverged beam to be collimated and directed to therapeutic application. The beam, first diverged and then collimated, is dimensionally larger with a relatively reduced intensity or radiant fluence, improving its suitability for use in therapeutics.

The hand-held therapeutic laser apparatus of this disclosure thus has a special opto-mechanical construction, which enables changeability of a front collimating lens to create different effective laser apertures. A smaller effective aperture has a comparatively higher radiant flux density for treatment of a small area that requires a higher energy dose, while a larger effective aperture facilitates treatment of a large area at a relatively reduced radiant intensity. The user is able to regulate laser dosimetry to the treated area by changing-out a lens head assembly to adjust the effective laser aperture by varying the radiant flux emitted by the apparatus.

Figure 1:
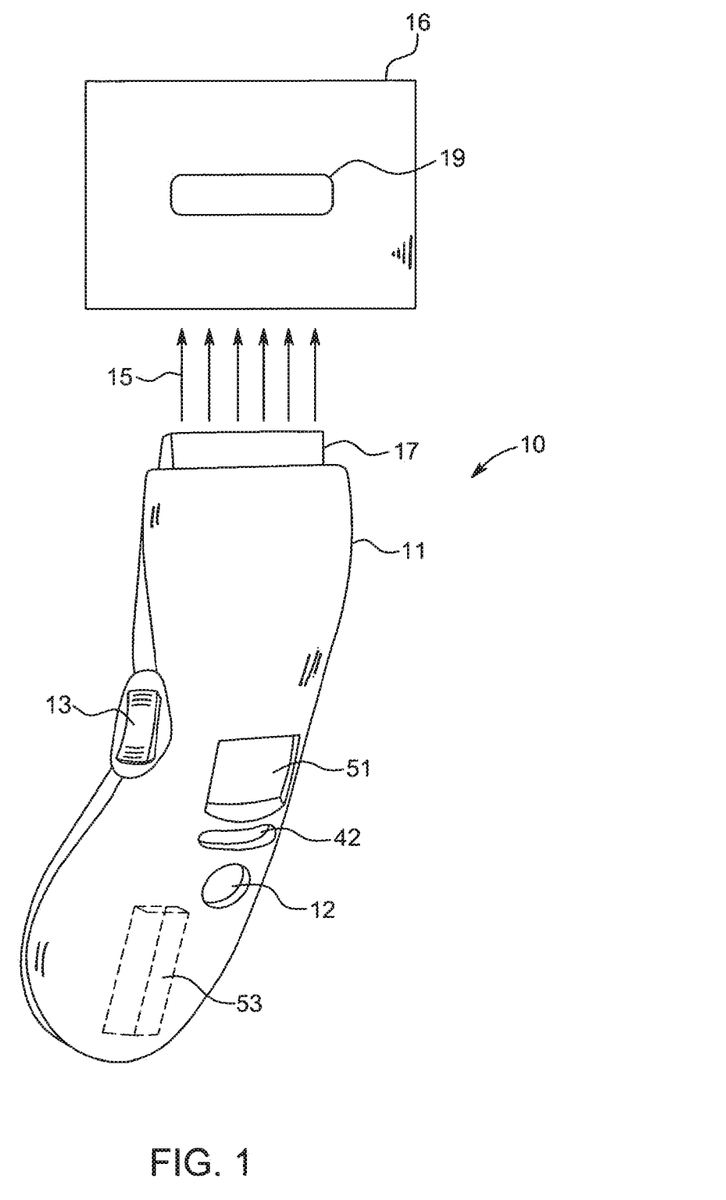
FIG. 1 is a diagrammatic illustration of a hand-held low-level laser therapy apparatus according to the present disclosure, showing the emission of a collimated from the apparatus to define an illuminated area on a treatment surface; in the figure, the treatment surface is depicted in a position rotated relative to the apparatus.

FIG. 1 is a schematic illustration of a handheld low-level laser therapy apparatus 10 for performing laser therapy, according to an exemplary embodiment of the invention. In an exemplary embodiment of the invention, apparatus 10 provides as output an elongated monochromatic substantially coherent laser beam 15 that is collimated by a lens (not shown) directly from the naturally diverging beam emitted by a laser diode within the apparatus 10. FIG. 1 shows the laser-illuminated area 19 that is defined upon an object surface 16 (e.g., a portion of a patient's skin) by the impingement of the beam 15; the area 19 is generally elliptical or rectangular in shape. In contrast to prior art devices, instead of focusing the laser beam from the laser diode to a single spot to provide a stronger illumination on that spot, the present system exploits the natural tendency of the laser diode to cast a diverging beam to form an elongated beam to cover a larger targeted area 19.

For clarity of illustration in FIG. 1, the object surface 16 is rotated (e.g. 90 degrees) with respect to the directional axis of propagation of the final beam 15. The FIG. 1 nevertheless depicts how, in one preferred embodiment, the final beam defines in a plane (i.e., 16) perpendicular to the direction of propagation of the beam 15 an elongated illuminated area 19, in which the length of the illuminated area is at least twice the width of the illuminated area.

A standard laser diode in use in medical devices typically has a first angle of divergence of about 5 to 10 degrees along its width, and a second angle of divergence of about 30 to about 40 degrees along its length. Instead of using a lens to correct the beam to a narrow beam, the present apparatus 10 employs a lens to form a collimated elongated beam 15 to cover a larger area 19, for example a treated area of about 3 cm to about 6 cm by about 0.5 to 1 cm. In an exemplary embodiment of the invention, the length of the illuminated area 19 is at least twice the width of the illuminated area 19. Further, the resulting elongated beam 15 is essentially coherent, having a light beam with an essentially common phase as accepted for laser diode emission.

By illuminating a comparatively larger area 19, the present system illuminates each particular point in the targeted object area with a weaker and safer laser beam (for example an eye safe beam having an intensity which is not hazardous to a person's eye). More power can be delivered more accurately to a specific area by illuminating for a longer time, or increasing the intensity of the laser diode, without the user's having to move the apparatus 10 during therapy. In the contrasting use of a known single-spot type laser, a single point is illuminated intensely and an object area targeted for treatment is processed by moving the device to shift the beam across the user's skin—thus illuminating intensely (but presumably briefly and periodically) each particular point in the target area.

In an exemplary embodiment of the invention, for example as seen in FIG. 1, the light sources and electronic circuitry for powering the apparatus 10 are encased in an ergonomic encasement 11 designed to fit into a user's hand. Optionally, the apparatus 10 includes an on/off switch 12, which turns the apparatus 10 on and off. When apparatus 10 is in the "on" state, it may be activated by pressing an activation switch 13 located on the side of encasement 11. Alternatively or additionally, apparatus 10 may be activated by pushing on or more eye safety activation switches, located on the distal or projection end 17 of the apparatus, against the person or object being radiated while using the apparatus 10. Activation when pressing against the person being radiated increase the safety of the apparatus, because it will not accidentally allow a user to shine light into the user's eye.

In preferred embodiments of the invention, apparatus 10 is powered by an internal power source (e.g. batteries 53). Alternatively or additionally, the apparatus can be powered by an external power source via a power-cable (not shown) that is plugged into an external power source, such as a household power socket. Optionally, when the device is plugged into an external power source the batteries may be recharged.

In some embodiments of the invention, apparatus 10 includes a display 51, for example an LCD display, which shows various information, such as the status of the battery, and/or a timer/counter. In an exemplary embodiment of the invention, the timer on display 51 is set by the user to a pre-selected value using a selector switch 42 of any suitable type; the value may represent an amount of time in seconds during which the apparatus will remain active when activated by the user. The apparatus may count down and deactivate automatically once it counts the pre-selected amount of time. For example if the user wishes to illuminate an object area for a specific amount of time, he sets the timer with the desired amount of time and activates the apparatus 10. The apparatus 10 illuminates the targeted object area until the time expires.

Thus, a basic embodiment of the apparatus according to the present disclosure is a hand-held laser apparatus having a laser diode that is adapted to produce a divergent monochromatic laser beam, and a front lens adapted to receive the divergent beam directly from the laser diode and exploit the natural beam divergence of the laser diode to form an essentially coherent monochromatic, collimated output beam 15, wherein the formed beam defines on a plane perpendicular to the direction of propagation of the beam an elongated illuminated area 19 in which the length of the illuminated area (greater dimension of area 19) is at least twice the size of the width (shorter dimension of area 19) of the illuminated area. The apparatus has a controller (e.g., switch 13) that is adapted to control activation of the laser diode. The encasement 11 encloses the laser diode, the lens and the controller, and is adapted to be hand-held. The optical-mechanical configuration of the apparatus allows a changing of the front lens, and thus of the effective aperture and radiant intensity of the output beam 15, in manners to be described further.

In all embodiments of the disclosed apparatus, there is a base assembly that mounts and includes the laser diode and, optionally, other optical components such as selected correction and/or divergent lenses. A base assembly connected in the projecting end of the apparatus hosing or encasement. All embodiments also feature at least one, preferably two or more, lens head assemblies. Each head assembly is a structural assembly mounting a front or collimating lens, which subtends a diverging beam and creates the therapeutic coherent beam that is controllably aimed at the area to be treated. The head assembly(ies) is removably attachable to the base assembly for optical cooperation with it.

Figure 2A:
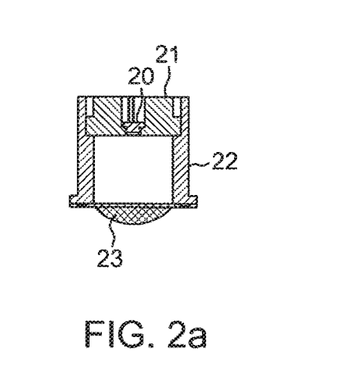
FIG. 2A is a transverse sectional view of a first lens head assembly, carrying a front lens, engaged with a base assembly mounting a laser diode, in accordance with a preferred embodiment of the present invention.
Figure 2B:
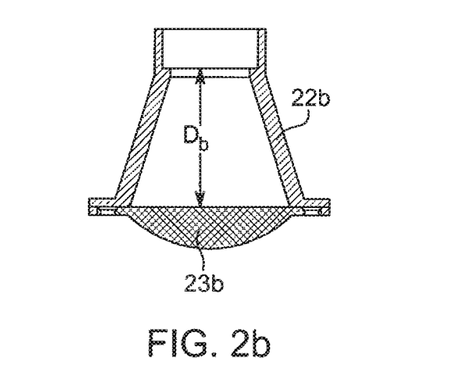
FIG. 2B is a transverse sectional view of a second lens head assembly, engageable with the base assembly depicted in FIG. 2A, according to a preferred embodiment of the invention.
Figure 2C:
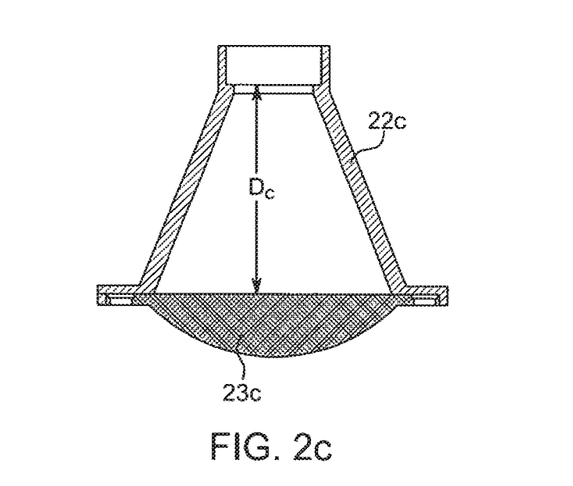
FIG. 2C is a transverse sectional view of a third lens head assembly, engageable with the base assembly depicted in FIG. 2A, according to a preferred embodiment of the invention.

Attention is invited to FIGS. 2*a-c* and 4*a-c*, which describe the mechanical and optical arrangements in accordance with a first embodiment of the invention according to the present disclosure. FIGS. 2*a-c* provide information about the mechanical assemblies, while FIGS. 4*a-c* offer information regarding optical beam patterns. This first embodiment enables a changing of the lens and effective aperture of the hand-held laser apparatus 10.

Figure 6:
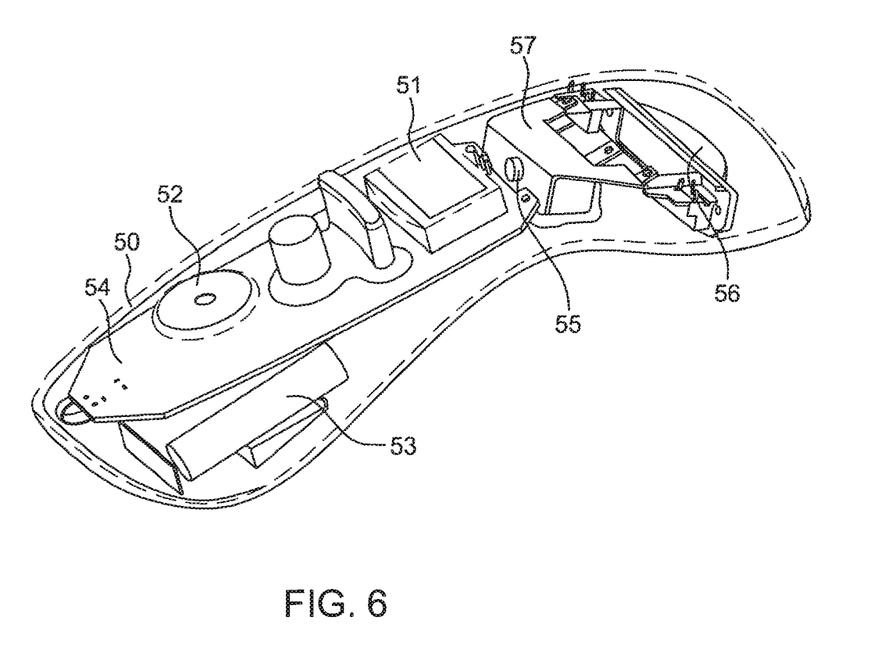
FIG. 6 is a partially transparent view of a hand-held low-level laser therapy apparatus according to this disclosure and similar to the embodiment of FIG. 1, showing additional features of the invention.

There is provided according to this disclosure mechanical assemblies attachable at, on, or near the projection end 17 of a hand-held apparatus 10 such as those seen in FIGS. 1 and 6. The assemblies are detachably provided, by any suitable attachment means such as screwed connections or clips, within or on the encasement 11 so as to controllably affect the dimensions of the emitted beam 15 and thus the effective aperture of the apparatus 10.

Figure 4A:
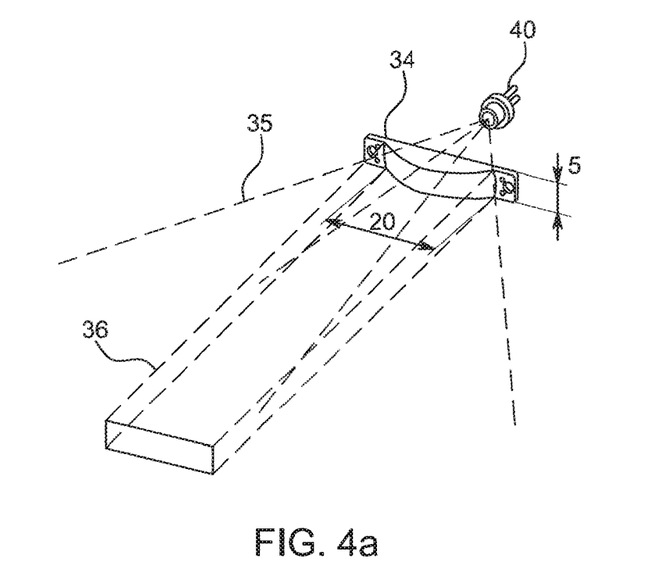
FIG. 4A is a perspective schematic view of an optical system in accordance with a preferred embodiment of the invention, showing a first collimating lens located at a first position in front of a laser diode emitting a multi-directionally diverging output beam, the lens intercepting the output beam to provide an effective laser aperture with a final beam having a first set of lateral dimensions and a flux density.
Figure 4B:
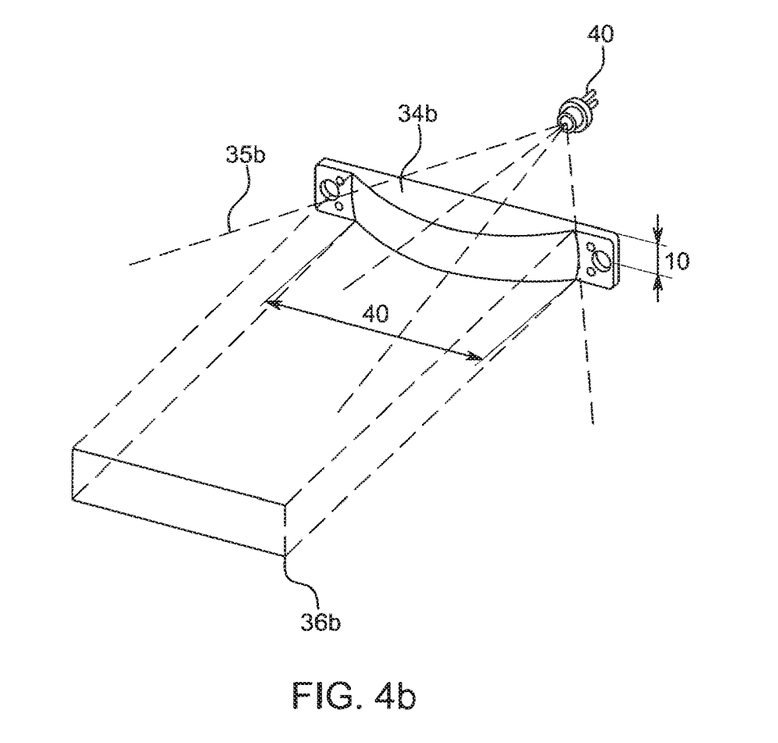
FIG. 4B is a perspective schematic view of an optical system in accordance with the embodiment of FIG. 4A, showing a second collimating lens located at a second position in front of a laser diode emitting a multi-directionally diverging output beam, the lens intercepting the output beam to provide an effective laser aperture with a final beam having a second set of lateral dimensions and a second flux density.
Figure 4C:
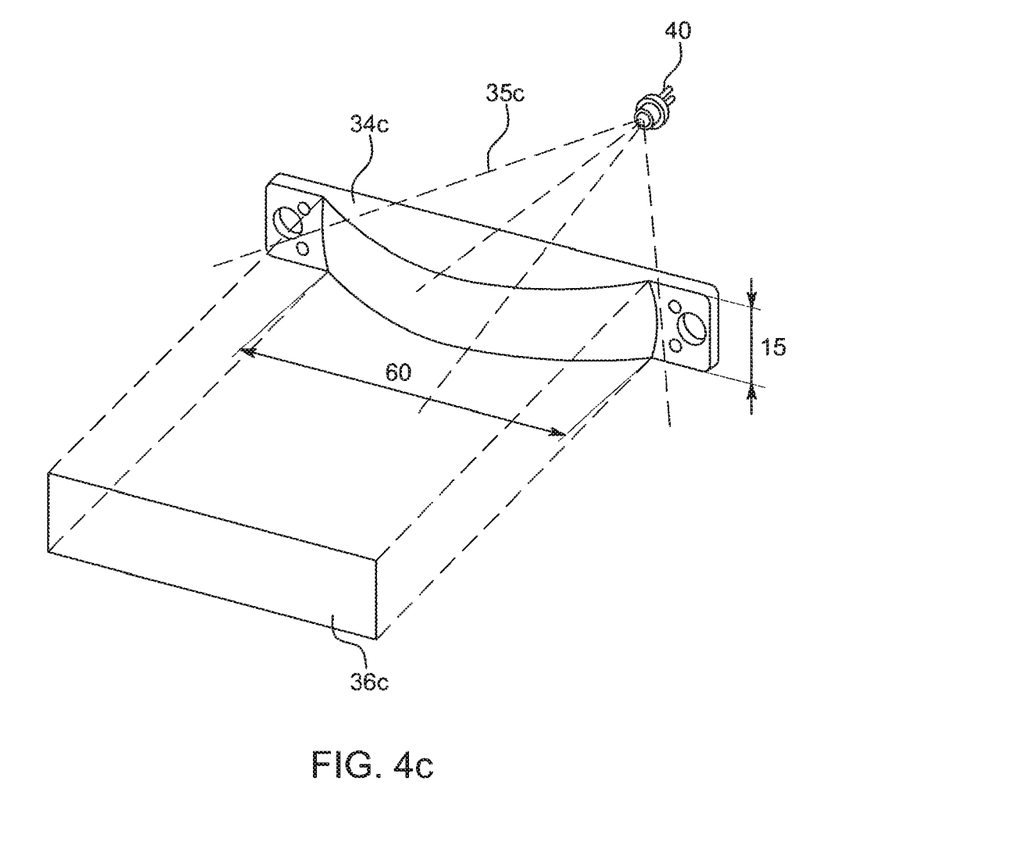
FIG. 4C is a perspective schematic view of an optical system in accordance with the embodiment of FIG. 4A, showing a third collimating lens located at a third position in front of a laser diode emitting a multi-directionally diverging output beam, the lens intercepting the output beam to provide an effective laser aperture with a final beam having a third set of lateral dimensions and a third flux density.

Reference is invited to FIG. 4*a*. The laser diode 40 has a diverging output beam 35 with a first angle of divergence of approximately 10° in one direction (i.e., in a vertical plane as depicted in FIGS. 4*a-c*) and a second angle of divergence of approximately 40° in the direction perpendicular to the first direction (i.e., in a horizontal plane as depicted in FIGS. 4*a-c*). The general boundary of the originally diverging output beam 35 is illustrated with two pairs of angled phantom lines diverging in vertical and horizontal planes from the diode 40 in FIGS. 4*a-c*; the first or smaller angle of divergence is in a vertical plane, while the larger, second angle of divergence is in the horizontal plane, the principle dimension of the lens 34, 34*b*, 34*c* also being arranged at the horizontal. The divergence creates an approximately elliptically shaped beam. Lens 34 preferably is a toroidal lens which corrects the laser astigmatism, and as seen in FIG. 4 has a generally rectangular shape (in a cross section orthogonal to the axis of beam propagation). FIGS. 4a-c indicate how in one embodiment of the invention the toroidal lens 34, 34b, or 34c is oriented relative to the diode 40 so that the lens's minor dimension is generally aligned with the first (smaller) angle of divergence, and the lens's major dimension is generally aligned with the second (larger) angle of divergence. The lens 34 intercepts and modifies the originally emitted diverging beam 35 to create a generally rectangular final beam 36. The size of the modified final beam 36 can be controllably changed by moving the lens 34 further from or closer to the laser diode 40. The lens 34 is designed, according to known optical principles, with a size such that in all its operating positions on an apparatus 10 it intercepts or captures the diverging original beam 35.

FIGS. 4a, 4b, and 4c show examples of such a design, with progressively larger lenses 34, 34b, 34c, and with their respective created collimated final beams (36, 36b, 36c) manifesting lateral dimensions of, for example, first vertical dimensions of for example 5, 10, and 15, (e.g. millimeters) and second or horizontal dimensions of for example 20, 40, 60. As suggested by the figures, a larger lens (e.g. 34b or 34c) typically is disposed in the system correspondingly farther (in FIGS. 4b-c, respectively) from the laser diode 40 along the principal axis of beam transmission. The effective aperture of an apparatus 10, as characterized by the dimensions (orthogonal to the principal axis of beam transmission) of the collimated final beam 36, 36b, or 36c created by the collimating lenses accordingly can be regulated or adjusted. By switching out on a base assembly different interchangeable head assemblies, a first final beam may be generated having a lateral beam dimension different from a corresponding lateral dimension of a second final beam created by another head assembly. A lateral beam dimension is a beam dimension (e.g. vertical or horizontal as suggested in FIG. 4a-c) measured in a plane perpendicular to the axis of principal beam transmission.

FIG. 2a shows the mechanical aperture-changing assembly for an embodiment of a multi-aperture laser apparatus according to this disclosure, including details regarding the configuration of the assembly relating with the optics of FIG. 4. In a mechanical aperture-changing assembly, the laser diode 20 is mounted on a base 21 which serves as a mechanical reference or base for the interchangeable front head lens mount 22, which in turn includes the front lens 23 for the assembly. The front lenses 23, 23b, and 23c seen in FIGS. 2a-c respectively, preferably are toriodal lenses shaped generally as shown. The base 21 is situated appropriately in the apparatus 10. Referring to FIG. 6, for example, the base 21 of FIG. 2a may correspond functionally to the base 57, and the lens 23 of FIG. 2a may correspond to the lens 56 seen in FIG. 6. In the illustrated embodiment, the base 21 also functions as a beneficial heat sink. The laser diode 20 (corresponding generally to diode 40 in FIGS. 4a-c and diode 55 in FIG. 6) is provided on the base 21. The front lens 23 (corresponding to lens 34 in FIG. 4a) is disposed on the changeable lens mount 22.

Combined reference to FIGS. 2a-c provides examples of how an interchangeable changeable front head assembly, including the lens mount 22 and front lens 23, permit the effective aperture of a hand held laser apparatus (i.e., 10, 50) to be adjusted by controllably changing the size of the collimating lens and its distance from the laser source 20. In FIG. 2a, the front lens 23 of a selected optical characteristic has first selected dimensions, and is carried by the lens mount 22. The lens mount 22 is configured to as to dispose the front lens 23 a predetermined distance from the laser source 20 when the changeable front head assembly is engaged upon the base 21. The lens mount 22 is adapted to receive and hold the particular front lens 23 having the desired optical characteristics, including lens dimensions. The lens mount 22 is removably engageable (as by, for example only, a clip or threaded screwed connection) with the heat sink base 21 mounting the laser diode 20. When it is desired to change the size and/or intensity of the final beam (e.g., beam 36 in FIG. 4a, corresponding to beam 15 in FIG. 1), the first front head assembly is removed from the base 21, and replaced with an interchangeable second front head assembly, such as that seen in FIG. 2b. The second front head assembly has a lens mount 22b that is removably engageable with the base 21 in the same manner as the first lens mount 22. The second lens mount 22b has a greater axial dimension, however, in a manner so as to locate the front lens 23b a relatively greater (predetermined) distance Db from the laser diode 20 (FIG. 2b). Further, as indicated in FIG. 2b, the second lens mount 22b typically mounts a second front lens 23b having optical characteristics (for example, principal dimensions) distinct from the characteristics of the first front lens 23 of FIG. 2a. FIG. 2c provides additional information regarding the advantages of the invention. The third front head assembly seen in FIG. 2c also is removably connectable to the base assembly 21. For example, combined reference to FIGS. 2a-c shows that the first, second, and third front head assemblies all have base barrel portions of substantially equal inside diameters, which inside diameters are slightly larger than the outside diameter of the base assembly 21. Thus the front head assemblies are essentially interchangeable with respect to the base assembly 21, such that any one of them is disposable around, to be removably engageable with, the base 21. FIG. 2c shows that the third lens mount 22c positions a third front lens 23c, of a comparatively even larger size, a relatively greater distance Dc from the laser diode 20, which remains in an unchanged location and position in the base 21.

It is understood that any suitable means for detachably connecting a head assembly including a lens mount (22, 22b, 22c) to a base assembly may be utilized in the practice of the invention.

From the foregoing, it is apparent that the effective aperture of a hand held therapeutic laser apparatus can be selectively changed, so as to controllably adjust the actual size (and radiant flux) of the final collimated beam 36 (i.e., beam 15 in FIG. 1). The lens 23 can be changed out to be larger, and further from the laser beam source, due to the divergent character of beam as originally emitted from the diode. The size of the area 19 illuminated on the object surface 16 thus may be regulated by the user by deploying two or more interchangeable front head assemblies.

Thus, and as more fully disclosed in co-pending senior U.S. patent application Ser. No. 12/534,878, there is provided in the present apparatus system a laser diode that is adapted to produce a monochromatic laser beam, which may be an infrared laser. At least one lens in the system is adapted to receive the original beam directly from the laser diode, and is sized, located and shaped to exploit the natural divergence of the beam emitted from the diode to form a substantially coherent monochromatic, collimated beam of reduced flux density. The beam (e.g. beam 15) formed by the at least one lens is adapted to form, on a plane (e.g. surface 16) generally perpendicular to the direction of beam propagation an elongated illuminated area (e.g. area 19). The length of the elongated illuminated (elliptical/rectangular) area preferably is at least twice the size of the width of the illuminated area.

An encasement mostly encloses the laser diode, the front collimating lens and a controller or switching adapted to control activation of the laser diode. The encasement is adapted to be hand held by the user. The lens may be a toroidal lens having differing or varying lens radii, in the direction producing the length of the illuminated area and in the direction producing the width of the illuminated area respectively. An aspect of the optical system of the invention is that the front lens is sized, shaped, and located so as to receive intercept a substantial majority or all a divergent emitted beam, so as to collimate the divergent beam and direct it to the area 19 of interest.

Figure 3A:
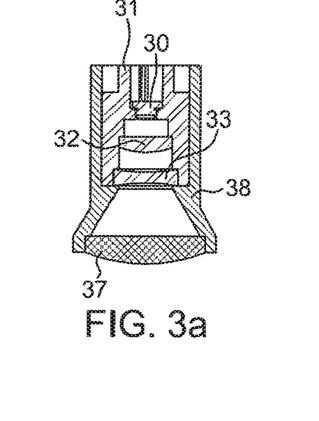
FIG. 3A is a transverse sectional view of a first lens head assembly, carrying a front lens, engaged with a base assembly mounting a laser diode and other optics, in accordance with an alternative embodiment of the present invention.
Figure 3B:
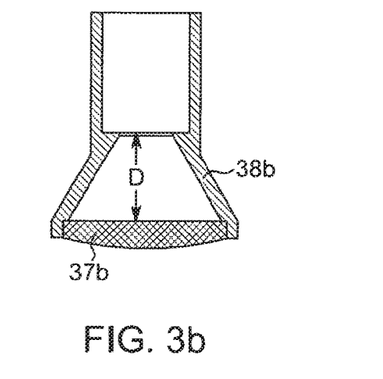
FIG. 3B is a transverse sectional view of a second lens head assembly, engageable with the base assembly depicted in FIG. 3A, according to an alternative embodiment of the invention.
Figure 3C:
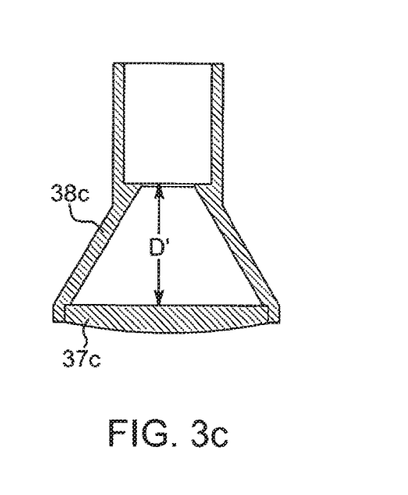
FIG. 3C is a transverse sectional view of a third lens head assembly, engageable with the base assembly depicted in FIG. 3A, according to an alternative embodiment of the invention.
Figure 5A:
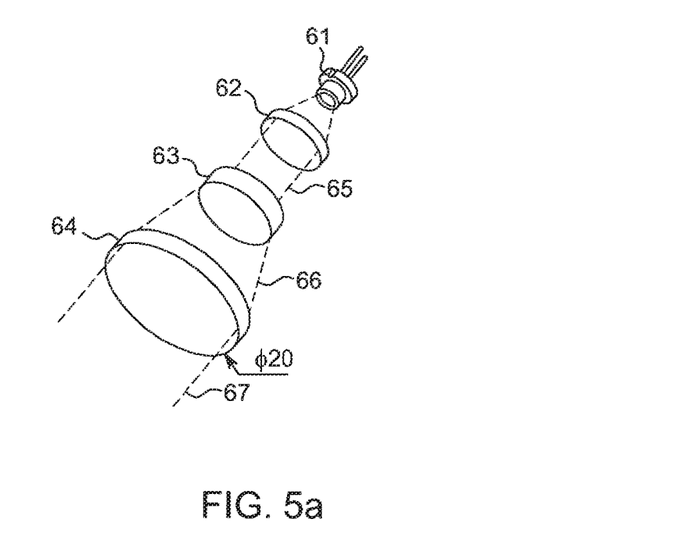
FIG. 5A is a perspective schematic view of an optical system in accordance with an alternative embodiment of the invention, showing a first collimating lens located at a first position in front of an optical subsystem emitting an approximately circular diverging beam, the collimating lens intercepting the diverging beam to provide an effective laser aperture with an approximately circular final beam having a first diameter and a flux density.
Figure 5B:
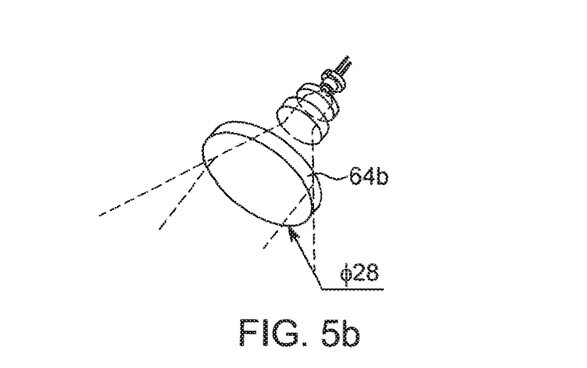
FIG. 5B is a perspective schematic view of an optical system in accordance with the embodiment of FIG. 5A, showing a second collimating lens located at a second position in front of the optical subsystem of FIG. 5A emitting an approximately circular diverging beam, the second collimating lens intercepting the diverging beam to provide an effective laser aperture with an approximately circular final beam having a second diameter and a second flux density.
Figure 5C:
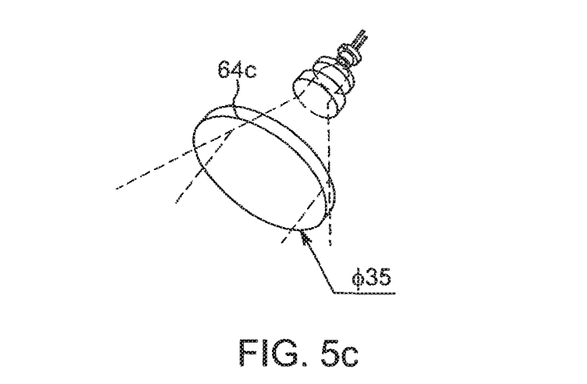
FIG. 5C is a perspective schematic view of an optical system in accordance with the embodiment of FIG. 5A, showing a third collimating lens located at a third position in front of the optical subsystem of FIG. 5A emitting an approximately circular diverging beam, the third collimating lens intercepting the diverging beam to provide an effective laser aperture with an approximately circular final beam having a third diameter and a third flux density.

Reference is made to FIGS. 3 and 5, which are respectively the mechanical and the optical configurations of a possible second embodiment of a system according to this disclosure. In this embodiment, a laser correction lens is employed to collimate the diverging beam originally emitted from the laser diode, and to direct the resulting coherent beam to a divergent lens. The beam propagating from the divergent lens has relatively reduced radiant flux, and is then intercepted by a front collimating lens, for coherent transmission to the targeted surface. The laser diode, laser correction lens, and divergent lens preferably are arranged in a base, and the front collimating lens is disposed in a head assembly removably attachable to the base. In this alternative embodiment, the lenses may be configured so to generate a generally circular, rather than elliptical-rectangular final, substantially coherent, beam.

Regarding the optics of this alternative embodiment, the laser diode 61 in FIG. 5*a* emits a beam with a dimensional ratio of, for example, about 1:4 in the first (parallel) and second (perpendicular) directions. Lens 62 is a laser correction lens which corrects the astigmatism of the laser diode and its generated original beam; the corrective lens emits an approximately parallel first coherent beam 65. A suitable such laser correction lens 62 is commercially available from CVI Melles Griot, Albuquerque, N.Mex. 87123, USA. Lens 63, in front of the correction lens, is a divergent lens which preferably creates an approximately circular second diverging beam 66. The front collimating lens 64 in FIG. 5*a* modifies the second diverging beam 66, and creates an approximately coherent final beam 67. As suggested by FIGS. 5*a-c*, the front collimating lens 64 can be provided in different sizes, and positioned at different distances from the divergent lens 63. The size of the collimating lens 64 in each deployment distance is designed to capture substantially all the second diverging beam 66 emitted from the divergent lens 63. Such a configuration, whereby most or all the second diverging beam 66 is intercepted and collimated, enables the collimating lens 64 to be changed (and its position changed) in a deliberate manner to create a smaller or larger effective aperture (i.e., corresponding to the diameter of the finally created mostly coherent beam 67), according to the desired treatment area (e.g., illuminated area 19 in FIG. 1).

FIG. 3 supplies details regarding the mechanical configuration of the system relating with the optics of FIGS. 5*a-c*. The laser diode 30 (corresponding generally to diode 61 in FIG. 5*a*), the correction lens 32 (corresponding generally to correction lens 62 in FIG. 5*a*) and divergent lens 33 (e.g., corresponding to lens 63 in FIG. 5*a*) are assembled together in mechanical base assembly 31. The base assembly may be within, for example, an encasement 11 similar to that of FIG. 1, near the projecting end 17 of the apparatus 10. The head assembly includes a front collimating lens 37 (e.g. lens 64 in FIG. 5*a*, corresponding functionally to a lens in, for example, an apparatus 10 similar to that of FIG. 1) disposed on a changeable lens mount 38.

Combined reference to FIGS. 3*a*-c provide examples of how an interchangeable front head assembly including a lens mount 38 and front collimating lens 37 permit adjustability in the size of the collimating lens and its distance from the divergent lens 33. In FIG. 3*a*, the front collimating lens 37 has a first selected diameter, and is carried by the lens mount 38. The lens mount 38 is adapted to receive and hold the particular collimating lens 37 having the desired optical characteristics, including, e.g., diameter. The lens mount 38 is removably engageable (as by, for example only, a clip or friction connection, or by threaded screwed engagement) with the mechanical base assembly 31 containing other optical elements of the apparatus. When it is desired to change the size and/or intensity of the final substantially coherent beam (e.g., beam 67 in FIG. 5*a*), the first head assembly is removed from the base assembly 31, and replaced with an interchangeable second front head, such as that seen in FIG. 3*b*. The second front head has a lens mount 38*b* that is removably engageable with the mechanical assembly in the same manner as the first lens mount 38. The second lens mount 38*b* has, in the example of FIG. 3*b*, a greater axial dimension, however, in a manner so as to locate the collimating lens 37*b* a relatively greater distance D from the divergent lens 33 (FIG. 3*b*) (and thus from the source laser diode 30). Further, as indicated in FIG. 3*b*, the second lens mount 38*b* mounts a second collimating lens 37*b* that ordinarily has different optical characteristics (for example, diameter) distinct from the characteristics of the first front collimating lens 37 of FIG. 3*a*. FIG. 3*c* provides additional illustration in this regard. The third front head assembly seen in FIG. 3*c* also is removably connectable to the base assembly 31. For example, combined reference to FIGS. 3*a-c* shows that the first, second, and third head assemblies all respectively have base barrel portions of substantially equal inside diameters, which inside diameters are slightly larger than the outside diameter of the base assembly 31. Thus the heads assemblies are essentially interchangeable with respect to the base assembly 31, such that any one of them is disposable around, to be removably engageable with, the base assembly. FIG. 3*c* shows that the third lens mount 38*c* positions a third collimating lens 37*c*, having (for example) a comparatively even larger diameter, a relatively greater third distance D' from the divergent lens 33 (which remains in an unchanged location and position in relation with the base assembly 31.

It is observed, therefore, that by removing and replacing on a base assembly different interchangeable head assemblies, a first final beam 67 may be generated having a lateral beam dimension different from a corresponding lateral dimension of a second final beam created by another head assembly. FIGS. 5*a-c* illustrate by way of example adjusted final beam diameters of 20 mm, 28 mm, and 35 mm, generated by respective collimating lenses of correspondingly larger respective sizes and distances from the base assembly.

It is understood that any suitable means for detachably connecting a head assembly including a lens mount (38, 38*b*, 38*c*) to a base assembly may be utilized in the practice of the invention.

Thus, the effective aperture of a hand held therapeutic laser apparatus can be selectively changed, so as to controllably adjust the actual size (and radiant energy fluence) of the final collimated beam 67 (i.e., beam 15 in FIG. 1) created by the collimating lens. The front collimating lens 37 can be changed out to be larger, and further from the laser beam source, due to the character of the diverging beam 66 received from the divergent lens 63. The size of the area 19 illuminated on the object surface 16 thus may be regulated by the user by deploying two or more interchangeable front head assemblies.

FIG. 6 shows generally a complete hand-held laser apparatus 50 generally in accordance with the embodiments described above. The laser apparatus 50 incorporates within its interior a printed electronic circuit board 54, with the required electronics (known in the art) to drive the laser diode and control the operation of the laser apparatus. The lens 56 (e.g., corresponding to lens 34 in FIGS. 4a-c) is positioned in front of the laser diode 55, which is mounted on heat sink base 57.

The laser apparatus 50 preferably includes thereon a readily visible LCD display 51 which shows the apparatus cumulative or timed operating time, and user warnings regarding the statuses of the laser and battery 53. The apparatus 50 preferably is powered by internally housed rechargeable batteries 53. The apparatus 50 also optionally includes audio warnings or indicators indications available by a speaker or buzzer 52.

In summary of the foregoing, there is described a therapeutic laser apparatus 10, 50 having an encasement 11 adapted to be hand-held. There is base assembly in the encasement, which base assembly includes a laser diode (20, 30, 40, 55 or 61) for generating a monochromatic laser beam whereby a diverging laser beam is emitted from the base assembly.

At least two head assemblies are removably enagageable with the base assembly, and each head assembly features a lens mount (22, 22b, 22c, 38, 38b, or 38c) having an axial dimension and a collimating lens (23, 23b, 23c, 34, 34b, 34c, 37, 37b, 37c, 64, 64b, or 64c) on the lens mount for creating an approximately coherent final beam. In a preferred embedment, the axial dimension of any particular lens mount of a first one of the head assemblies is different from the axial dimension of the lens mount of any given second one of the head assemblies; similarly, the size of the collimating lens of that first head assembly is different from the size of the collimating lens of the second head assemblies. As a result, when the first one of the head assemblies is engaged with the base assembly, the collimating lens of the first head assembly intercepts, at a first distance (e.g. distance $D_b$ in FIG. 2b, or distance D in FIG. 3b), the diverging beam emitted from the base assembly. When the second head assembly is engaged with the base assembly, the collimating lens of the second head assembly intercepts, at a second distance (e.g. distance $D_c$ in FIG. 2c, or distance D' in FIG. 3c), the diverging beam emitted from the base assembly. Consequently, the first head assembly when in use with the base assembly creates a first final beam (e.g., beam 36b or beam 67b) having a lateral beam dimension different from a corresponding lateral dimension of a second final beam (e.g., beam 36c or beam 67c) created by the second head assembly when in use with the base assembly.

The head assemblies preferably are a plurality of head assemblies that are interchangeable in relation to a particular base assembly. Any one of the head assemblies when in use with the base assembly preferably emits a coherent final beam having a radiant flux different from the radiant flux emitted from any selected other one of the head assemblies when in use with that base assembly.

In an alternative embodiment of the apparatus, the base assembly includes a correction lens (32, 62) for correcting astigmatism in the diverging original beam emitted from the laser diode (40, 61) and for modifying the original beam to create a substantially circular coherent beam 65. In front of the correction lens is disposed a divergent lens (33, 63) for creating, from the generally coherent beam 65 created by the correction lens, the diverging laser beam 66 emitted from the base assembly, so that the diverging laser beam emitted from the base assembly is an approximately circular diverging beam.

In all embodiments, any one of the head assemblies when in use with a base assembly emits a coherent final beam having a radiant flux different from the radiant flux emitted from any other one of the head assemblies when in use with the base assembly. This is because when a first head assembly is used with the base assembly, it creates a first final beam having a lateral beam dimension different from a corresponding lateral dimension of any other, second, final beam created by another, different head assembly when in use with the base assembly.

Although the invention has been described in detail with particular reference to these preferred embodiments, other embodiments can achieve the same results. From the foregoing, those skilled in the art will recognize an advancement of this invention in the relevant field of art. While the invention has been described in relation to a preferred embodiment thereof shown in the accompanying drawings, it also is to be recognized that the same is readily susceptible to modification, variation and substitution of equivalents without avoiding the invention. The system and apparatus are not intended to be limited by the foregoing except as may appear in the following appended claims, and it is intended to cover in the claims all such modifications and equivalents.

What is claimed is:

1. A therapeutic laser apparatus comprising:
   an encasement adapted to be hand-held;
   a base assembly in the encasement, comprising a laser diode for generating a monochromatic laser beam whereby a diverging laser beam is emitted from the base assembly; and
   at least two head assemblies removably enagageable with the base assembly, each head assembly comprising:
      a lens mount having an axial dimension; and
      a collimating lens on the lens mount for creating a collimated, approximately coherent final beam;
   wherein the axial dimension of the lens mount of a first one of the head assemblies is different from the axial dimension of the lens mount of a second one of the head assemblies, and wherein a size of the collimating lens of the first one of the head assemblies is different from a size of the collimating lens of the second one of the head assemblies;
   whereby when the first one of the at least two head assemblies is engaged with the base assembly, the collimating lens of the first head assembly intercepts, at a first distance from the base assembly, the diverging beam emitted from the base assembly, and when the second one of the at least two head assemblies is engaged with the base assembly, the collimating lens of the second head assembly intercepts, at a second distance from the base assembly, the diverging beam emitted from the base assembly;
   wherein the first head assembly when in use with the base assembly creates a first final beam having a lateral beam dimension different from a corresponding lateral dimension of a second final beam created by the second head assembly when in use with the base assembly.

2. The apparatus according to claim 1 wherein:
the at least two head assemblies comprise a plurality of head assemblies interchangeable in relation to the base assembly; and
any one of the head assemblies when in use with the base assembly emits a collimated, approximately coherent final beam having a radiant flux different from a radiant flux emitted from any other of the head assemblies when in use with the base assembly.

3. The apparatus according to claim 1 wherein:
the diverging laser beam emitted from the base assembly is emitted directly from the laser diode, and propagates with a first angle of divergence and with a second angle of divergence greater than the first angle of divergence; and
the collimating lens is an oblong toroidal lens having a major dimension aligned with the second angle of divergence.

4. The apparatus according to claim 1 wherein the final beam forms on a plane perpendicular to the direction of propagation of the beam an elongated illuminated area in which the length of the illuminated area is at least twice the width of the illuminated area.

5. An apparatus according to claim 1 wherein the base assembly further comprises:
a correction lens for correcting astigmatism in a diverging original beam emitted from the laser diode and for modifying the original beam to create an approximately circular coherent beam; and
a divergent lens for creating, from the coherent beam created by the correction lens, the diverging laser beam emitted from the base assembly;
wherein the diverging laser beam emitted from the base assembly is an approximately circular diverging beam.

6. A handheld, low-level laser apparatus comprising:
a laser diode configured to generate an infrared (IR) laser emission having an astigmatism and propagating along a laser path;
one or more corrective lens positioned in the laser path and configured to receive the IR laser emission therethrough, the one or more corrective lens being further configured alone or in combination to correct the astigmatism of the IR laser emission and to collimate the IR laser emission;
a divergence lens positioned in the laser path after the one or more corrective lens and configured to receive the IR laser emission therethrough and to diverge the IR laser emission after the IR laser emission passes through the one or more corrective lens; and
a front lens positioned in the laser path after the divergence lens and configured to receive the IR laser emission therethrough and to collimate the IR laser emission after the IR laser emission passes through the divergence lens.

7. The apparatus of claim 6, wherein the one or more corrective lens is a toroidal lens.

8. The apparatus of claim 6, wherein the laser diode, the one or more corrective lens, and the divergence lens are comprised by a base assembly and the front lens is comprised by a front lens assembly configured to couple releasably to the base assembly to provide the front lens positioned in the laser path.

9. The apparatus of claim 8, further comprising a second front lens assembly configured to couple releasably to the base assembly interchangeably with the front lens assembly, the second front lens assembly including a second front lens positioned in the laser path after the divergence lens when the second front lens assembly is coupled to the base assembly, a distance between the second front lens and the divergence lens when the second front lens is coupled to the base assembly being different than a distance between the front lens and the divergence lens when the front lens assembly is coupled to the base assembly.

10. The apparatus of claim 9, further comprising a third front lens assembly configured to couple releasably to the base assembly interchangeably with the front lens assembly and the second front lens assembly, the third front lens assembly including a third front lens positioned in the laser path after the divergence lens when the third front lens assembly is coupled to the base assembly, a distance between the third front lens and the divergence lens when the third front lens is coupled to the base assembly being different than both a distance between the front lens and the divergence lens when the front lens assembly is coupled to the base assembly and a distance between the second front lens and the divergence lens when the second front lens assembly is coupled to the base assembly.

11. A low-level laser beam producing method comprising:
using a laser diode, generating an infrared (IR) laser emission having an astigmatism and propagating the IR laser emission along a laser path;
using one or more corrective lens positioned in the laser path, receiving the IR laser emission therethrough and, using the one or more corrective lens alone or in combination, correcting the astigmatism of the IR laser emission and collimating the IR laser emission;
using a divergence lens positioned in the laser path after the one or more corrective lens, receiving the IR laser emission therethrough and diverging the IR laser emission after the IR laser emission passes through the one or more corrective lens; and
using a front lens positioned in the laser path after the divergence lens, receiving the IR laser emission therethrough and collimating the IR laser emission after the IR laser emission passes through the divergence lens.

* * * * *